United States Patent
Kaneko et al.

(10) Patent No.: US 12,305,603 B2
(45) Date of Patent: May 20, 2025

(54) FUEL PROPERTY DETERMINATION DEVICE AND VEHICLE

(71) Applicants: Isuzu Motors Limited, Yokohama (JP); Nikki Co., Ltd., Kanagawa (JP)

(72) Inventors: Shinichiro Kaneko, Fujisawa (JP); Misao Tanaka, Yokohama (JP); Koji Goto, Fujisawa (JP); Buso Takigawa, Kanagawa (JP); Ryota Adachi, Kanagawa (JP)

(73) Assignees: Isuzu Motors Limited, Yokohama (JP); Nikki Co., Ltd., Kanagawa (JP)

( * ) Notice: Subject to any disclaimer, the term of this patent is extended or adjusted under 35 U.S.C. 154(b) by 0 days.

(21) Appl. No.: 18/701,654

(22) PCT Filed: Oct. 18, 2022

(86) PCT No.: PCT/JP2022/038757
§ 371 (c)(1),
(2) Date: Apr. 16, 2024

(87) PCT Pub. No.: WO2023/068267
PCT Pub. Date: Apr. 27, 2023

(65) Prior Publication Data
US 2024/0410329 A1    Dec. 12, 2024

(30) Foreign Application Priority Data
Oct. 18, 2021    (JP) .................................. 2021-170415

(51) Int. Cl.
*F02P 5/15*    (2006.01)
*F02D 19/02*    (2006.01)
(Continued)

(52) U.S. Cl.
CPC ............ *F02P 5/1502* (2013.01); *F02D 19/02* (2013.01); *F02D 41/0025* (2013.01);
(Continued)

(58) Field of Classification Search
CPC ......... F02P 5/1502; F02P 5/152; F02D 19/02; F02D 19/029; F02D 2200/0611;
(Continued)

(56) References Cited

U.S. PATENT DOCUMENTS

| 6,412,472 B1 * | 7/2002 | Tilagone ............... F02D 19/029 123/406.44 |
| 10,260,407 B2 | 4/2019 | Zhong et al. |

(Continued)

FOREIGN PATENT DOCUMENTS

| DE | 102016220023 A1 * | 4/2018 | ......... F02D 41/0027 |
| JP | 2012-082741 | 4/2012 | |

(Continued)

*Primary Examiner* — John M Zaleskas

(57) ABSTRACT

This fuel property determination device determines components of liquefied natural gas stored in a tank as a fuel for an engine. The fuel property determination device has: an estimation unit that estimates the methane number of the liquefied natural gas using a first estimation method when the engine is being driven, and estimates the methane number of the liquefied natural gas using a second estimation method different from the first estimation method when the engine is to be restarted from a stopped state; and a control unit that controls a notification device so as to provide a notification indicating that a property change has occurred in the liquefied natural gas, if the methane number of the liquefied natural gas estimated by the first or second estimation method is less than a threshold.

3 Claims, 4 Drawing Sheets

(51) Int. Cl.
*F02D 41/00* (2006.01)
*F02D 41/04* (2006.01)
*F02D 41/06* (2006.01)
*F02D 41/22* (2006.01)
*F02M 21/02* (2006.01)
*G01N 33/28* (2006.01)

(52) U.S. Cl.
CPC ....... *F02D 41/0027* (2013.01); *F02D 41/042* (2013.01); *F02D 41/062* (2013.01); *F02D 41/22* (2013.01); *F02M 21/02* (2013.01); *G01N 33/2835* (2013.01)

(58) Field of Classification Search
CPC .......... F02D 2200/0612; F02D 35/027; F02D 41/0027; G01N 33/2835
See application file for complete search history.

(56) References Cited

U.S. PATENT DOCUMENTS

| | | | | |
|---|---|---|---|---|
| 2008/0306672 | A1* | 12/2008 | Bauer | F02D 41/3035 |
| | | | | 123/295 |
| 2016/0208764 | A1* | 7/2016 | Mann | F02P 5/152 |
| 2017/0101948 | A1* | 4/2017 | Kunkel | F02B 43/04 |
| 2017/0218837 | A1* | 8/2017 | Zhong | F02B 43/12 |
| 2020/0355098 | A1* | 11/2020 | Rickert | F02D 19/029 |
| 2024/0352903 | A1* | 10/2024 | Goto | F02D 19/029 |
| 2024/0418140 | A1* | 12/2024 | Kaneko | F02D 45/00 |

FOREIGN PATENT DOCUMENTS

| | | | |
|---|---|---|---|
| JP | 2019138196 A * | 8/2019 | |
| JP | 2020159278 A * | 10/2020 | |
| JP | 2021-042734 | 3/2021 | |
| JP | 2021042734 A * | 3/2021 | |
| JP | 2021-092202 | 6/2021 | |
| JP | 2021131054 A * | 9/2021 | |
| KR | 10-2010-0058371 | 6/2010 | |
| KR | 20100058371 A * | 6/2010 | |
| KR | 20100063342 A * | 6/2010 | |
| WO | WO 2014/049646 | 4/2014 | |
| WO | WO-2022264795 A1 * | 12/2022 | |
| WO | WO 2023/068267 | 4/2023 | |

\* cited by examiner

FUEL PROPERTY DETERMINATION DEVICE AND VEHICLE

TECHNICAL FIELD

The present disclosure relates to a fuel property determination apparatus and a vehicle.

BACKGROUND ART

It is known, for example, that liquefied natural gas (LNG: hereinafter referred to as the LNG fuel) is used as a fuel for an engine in a vehicle or the like (for example, see Patent Literature (hereinafter referred to as "PTL") 1).

CITATION LIST

Patent Literature

PTL 1
Japanese Patent Application Laid-Open No. 2021-92202

SUMMARY OF INVENTION

Technical Problem

The LNG fuel is composed mainly of methane and contains components such as ethane, propane, and butane. In this case, methane having the lowest boiling point vaporizes first. Thus, a change in property (hereinafter referred to as a property change) occurs in the LNG fuel stored in a tank, and knocking is likely to occur in the engine.

It is therefore desirable that a property change in the LNG fuel be recognized by the user with more appropriate timing for the sake of measures against a property change in the LNG fuel (for example, fuel consumption, fuel exchange, or the like).

An object of one aspect of the present disclosure is to provide a fuel property determination apparatus and a vehicle each enabling the user to recognize a property change in the LNG fuel with more appropriate timing.

Solution to Problem

A fuel property determination apparatus according to one aspect of the present disclosure is a fuel property determination apparatus that determines a component of liquefied natural gas stored, as a fuel for an engine, in a tank. The fuel property determination apparatus includes: an estimation unit that estimates, in a case where the engine is being driven, a methane number of the liquefied natural gas by a first estimation method and estimates, in a case where the engine is restarted from a stopped state, the methane number of the liquefied natural gas by a second estimation method different from the first estimation method; and a control unit that controls, in a case where the methane number of the liquefied natural gas estimated by the first estimation method or the second estimation method is less than a threshold, a notification apparatus such that the notification apparatus provides a notification indicating that a property change has occurred in the liquefied natural gas.

A vehicle according to one aspect of the present disclosure includes the fuel property determination apparatus according one aspect of the present disclosure.

Advantageous Effects of Invention

According to the present disclosure, the user can recognize a property change in the LNG fuel with more appropriate timing.

DESCRIPTION OF EMBODIMENTS

Hereinafter, an embodiment of the present disclosure will be described with reference to the accompanying drawings.

Figure 1:
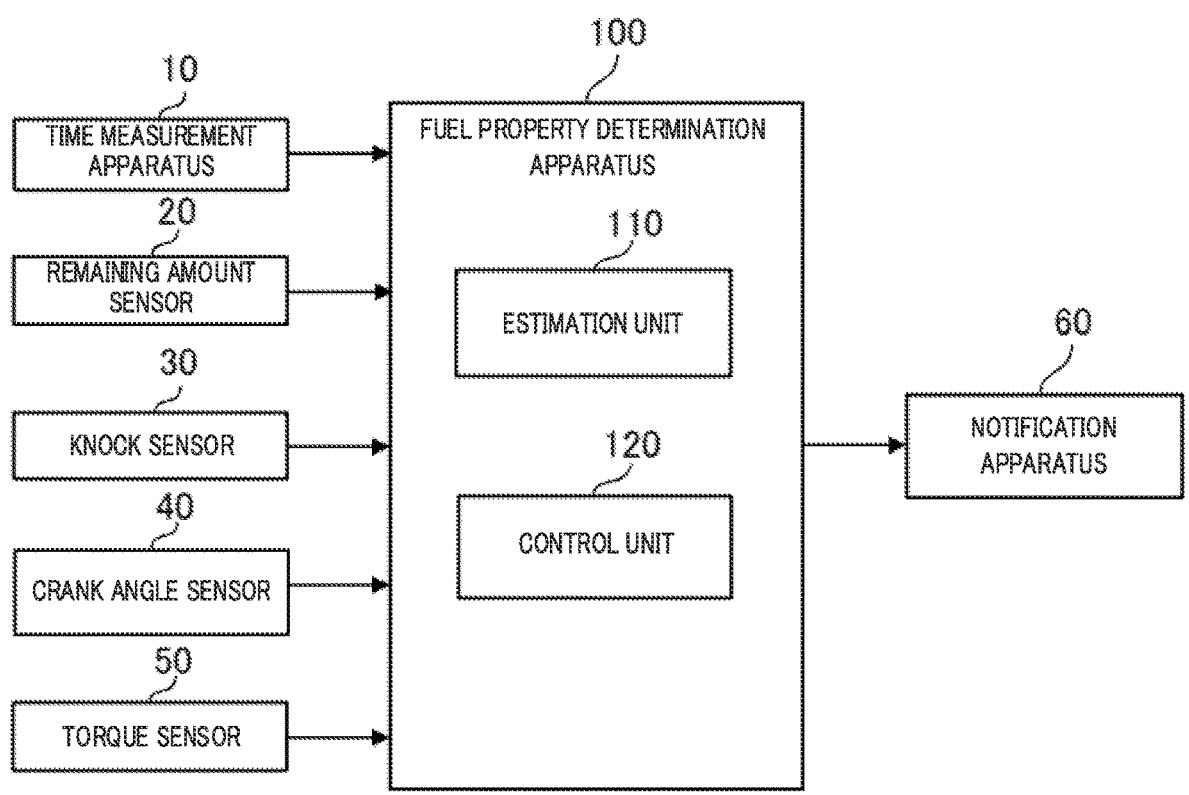
FIG. 1 schematically illustrates an exemplary configuration of a fuel property determination apparatus according to an embodiment of the present disclosure.

First, the configuration of fuel property determination apparatus 100 in the present embodiment will be described with reference to FIG. 1. FIG. 1 schematically illustrates an exemplary configuration of fuel property determination apparatus 100.

Fuel property determination apparatus 100 illustrated in FIG. 1 is mounted in, for example, a vehicle (not illustrated) including an engine (not illustrated) that is driven by the LNG fuel. This LNG fuel is, as described above, a fuel which contains a plurality of components (for example, methane, ethane, propane, butane, and the like) with boiling points different from each other, and in which a property change (for example, a change in the proportions of the plurality of components, which may also be referred to as a component change or an increase in the percentage of heavier components) may occur.

For example, an LNG fuel supply system (not illustrated) for supplying the LNG fuel to the engine is mounted in the vehicle. Although illustration is omitted, the LNG fuel supply system includes, for example, an LNG tank for storing the LNG fuel, an LNG fuel supply path, a carburetor for vaporizing the LNG fuel, an isolation valve for opening and closing the LNG fuel supply path, and an LNG regulator for reducing the pressure of the LNG fuel vaporized in the carburetor. The LNG fuel supply path connects the LNG tank to the LNG regulator via the isolation valve, and connects the LNG regulator to the engine. The engine is a spark-ignition internal combustion engine in which the vaporized LNG fuel is burned by ignition. The engine includes a plurality of cylinders.

Note that, in addition to the LNG fuel supply system described above, a CNG fuel supply system (not illustrated) for supplying compressed natural gas (CNG) to the engine may be mounted in the vehicle. Although illustration is omitted, the CNG fuel supply system includes, for example, a CNG tank for storing a CNG fuel, a CNG fuel supply path, an isolation valve for opening and closing the CNG fuel supply path, and a CNG regulator for reducing the pressure of the CNG fuel. The CNG fuel supply path connects the CNG tank to the engine via the isolation valve and the CNG regulator. In a case where the LNG fuel supply system and the CNG fuel supply system are mounted in the vehicle, it is possible to switch from the LNG fuel to the CNG fuel for use, for example, when the methane number of the LNG fuel decreases and the engine is in a high-load state.

Time measurement apparatus 10, remaining amount sensor 20, and notification apparatus 60 illustrated in FIG. 1 are mounted together with fuel property determination apparatus 100 in the vehicle, and are electrically connected to fuel property determination apparatus 100.

Time measurement apparatus 10 measures time (including, for example, year, month, day, hour, and minute). The measurement result of measurement apparatus 10 (hereinafter referred to as date and time information) is outputted from time measurement apparatus 10 to fuel property determination apparatus 100.

Note that, although a case where time measurement apparatus 10 is separate from fuel property determination apparatus 100 has been described as an example in the present embodiment, fuel property determination apparatus 100 may have the function of time measurement apparatus 10.

Remaining amount sensor 20 detects the remaining amount of the LNG fuel stored in the LNG tank. The detection result of remaining amount sensor 20 (hereinafter referred to as remaining amount information) is outputted from remaining amount sensor 20 to fuel property determination apparatus 100. Note that, the remaining amount may be the storage amount of the LNG fuel, or may be the ratio of the storage amount to the capacity of the entire LNG tank.

Knock sensor 30 detects knocking in the engine. Knock sensor 30 includes, for example, a piezoelectric element for detecting vibration of an engine block (not illustrated). The detection result of knock sensor 30 (hereinafter referred to as knocking information) is outputted from knock sensor 30 to fuel property determination apparatus 100.

Crank angle sensor 40 detects the engine speed. The detection result of crank angle sensor 40 (hereinafter referred to as speed information) is outputted from crank angle sensor 40 to fuel property determination apparatus 100.

Torque sensor 50 detects the engine load based on the degree of rotational fluctuation of a crankshaft (not illustrated), for example. Note that, the engine load may be detected based on the gas pedal position or the throttle position. The detection result of torque sensor 50 (hereinafter referred to as load information) is outputted from torque sensor 50 to fuel property determination apparatus 100.

Notification apparatus 60 provides a notification indicating that a property change has occurred in the LNG fuel (hereinafter referred to as the warning notification). Notification apparatus 60 is, for example, a display lamp provided, in the vehicle interior of the vehicle, in a position in which the display lamp is easily visible to an occupant in the vehicle (an example of the user). In this case, it is configured such that the flickering of the display lamp means that a property change has occurred in the LNG fuel.

Fuel property determination apparatus 100 is an apparatus that determines whether a property change has occurred in the LNG fuel stored in the LNG tank and, in a case where a property change has occurred in the LNG fuel, controls notification apparatus 60 such that notification apparatus 60 provides the warning notification.

Although illustration is omitted, fuel property determination apparatus 100 includes, as hardware, a central processing unit (CPU), a read only memory (ROM), in which computer programs are stored, a random access memory (RAM), which is a working memory, an input port, an output port, and the like, for example. Functions of fuel property determination apparatus 100 to be described later are implemented by the CPU executing, in the RAM, a computer program read from the ROM. Fuel property determination apparatus 100 may be implemented by, for example, an electronic control unit (ECU).

As illustrated in FIG. 1, fuel property determination apparatus 100 includes estimation unit 110 and control unit 120.

In a case where the engine is being driven, estimation unit 110 estimates the methane number of the LNG fuel (hereinafter, which may also be simply referred to as the methane number) by using a first estimation method.

When a brief description will be given of the first estimation method which will be described in detail later, in the first estimation method, estimation unit 110 calculates an ignition retard control amount for avoiding knocking in the engine, and estimates the methane number of the LNG fuel based on an index value indicating the ignition retard control amount.

In a case where the engine is restarted from a stopped state, on the other hand, estimation unit 110 estimates the methane number of the LNG fuel by using a second estimation method different from the first estimation method.

When a brief description will be given of the second estimation method which will be described in detail later, in the second estimation method, estimation unit 110 estimates the methane number of the LNG fuel based on the remaining amount of the LNG fuel in the LNG tank when the engine stops, and a stop time of the engine (an elapsed time from when the engine stops to when the engine restarts).

Control unit 120 determines whether the methane number of the LNG fuel estimated by the first estimation method or the second estimation method (hereinafter referred to as the estimated methane number) is less than a predetermined threshold.

In a case where the estimated methane number is less than the threshold, control unit 120 controls notification apparatus 60 such that notification apparatus 60 provides the warning notification.

For example, in a case where notification apparatus 60 is a display lamp, control unit 120 controls the display lamp such that the display lamp flickers at predetermined time intervals. Thus, the display lamp flickers, and the user (for example, an occupant in the vehicle) can easily recognize that a property change (which may also be referred to as an increase in the percentage of heavier components) has occurred in the LNG fuel.

Note that, in a case where the estimated methane number is not less than the threshold, control unit 120 does not control notification apparatus 60.

Next, the first estimation method will be described in detail.

First, estimation unit 110 calculates ignition retard control amounts in the plurality of cylinders, respectively, based on the knocking information acquired from knock sensor 30. Here, the ignition retard control amount refers to advance value $\Delta\theta(°)$ with respect to the ignition timing. Estimation unit 110 corrects the ignition timing of the spark plug for each cylinder based on the advance value (ignition retard control amount).

Here, in a case where advance value $\Delta\theta$ is 0, estimation unit 110 does not correct the ignition timing. In a case where advance value $\Delta\theta$ is $-\Delta\theta_1$, on the other hand, estimation unit 110 corrects the ignition timing such that the ignition timing is later than a predetermined ignition timing (an ignition timing at which correction is not performed) by $\Delta\theta_1$ (retarded by $\Delta\theta_1$). Further, in a case where advance value $\Delta\theta$ is $-\Delta\theta_2$, estimation unit 110 corrects the ignition timing such that the ignition timing is later than the predetermined ignition timing by $\Delta\theta_2$ (retarded by $\Delta\theta_2$). Here, in a case where the magnitudes of advance values $\Delta\theta$ are $0 > -\Delta\theta_1 > -\Delta\theta_2$, it is said that advance value (ignition retard control amount) $-\Delta\theta_1$ is lower than advance value 0. Further, it is said that advance value $-\Delta\theta_2$ is lower than advance value $-\Delta\theta_1$.

Next, estimation unit 110 calculates an average value of, among the acquired respective ignition retard control amounts in the plurality of cylinders, the respective ignition retard control amounts in two or more cylinders, where the respective ignition retard control amounts in the two or more cylinders are lower than the (respective) ignition retard control amount(s) in the other cylinder(s) among the plurality of cylinders.

For example, in a case where the advance values (ignition retard control amounts) in the plurality of cylinders are 0, $-\Delta\theta_1, \ldots, -\Delta\theta_{n-k}, -\Delta\theta_{n-(k-1)}, \ldots, -\Delta\theta_{n-1}, -\Delta\theta_n$, respectively, and the magnitudes of the advance values are $0 > -\Delta\theta_1 >, \ldots, -\Delta\theta_{-k} > -\Delta\theta_{n-(k-1)}, \ldots, > -\Delta\theta_{n-1} > -\Delta\theta_n$, respectively (where n and k are natural numbers), estimation unit 110 calculates an average value obtained by dividing the sum of the respective advance values $(-\Delta\theta_{n-(k-1)}, \ldots, -\Delta\theta_{n-1}, -\Delta\theta_n)$ in k cylinders by k, where the respective advance values $(-\Delta\theta_{n-(k-1)}, \ldots, -\Delta\theta_{n-1}, -\Delta\theta_n)$ in k cylinders are lower than the respective ignition retard control amounts in the other cylinders among the plurality of cylinders. In the following description, the average value of the respective advance values in k cylinders will be referred to as "index value".

Figure 2:
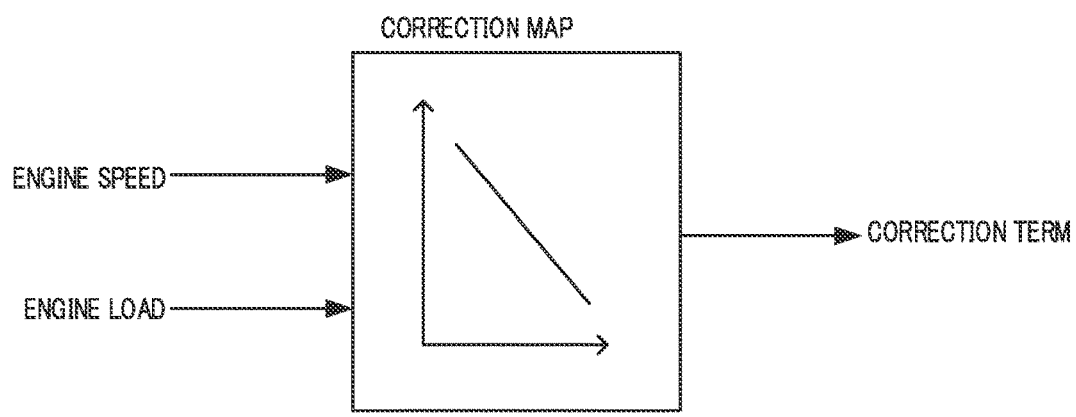
FIG. 2 schematically illustrates an image of correction term calculation.

Next, estimation unit 110 calculates a correction term for correcting the index value. FIG. 2 schematically illustrates an image of correction term calculation.

As illustrated in FIG. 2, estimation unit 110 calculates, based on the engine speed indicated in the speed information acquired from crank angle sensor 40 and the engine load indicated in the load information acquired from torque sensor 50, the correction term for the index value (average value) by referring to a correction map.

The correction map is stored in a storage unit (for example, the ROM (not illustrated)) of fuel property determination apparatus 100. The correction map is a map indicating the relationship of the engine speed and the engine load with the correction amount, and can be obtained by means of experiments and/or simulations.

The correction term is a parameter for modifying an index value (average value) at the time of the acquisition of the operation state (engine speed and engine load) to an index value of an operation state used as a reference (engine speed: 1000 rpm, engine load: 100 Nm).

Figure 3:
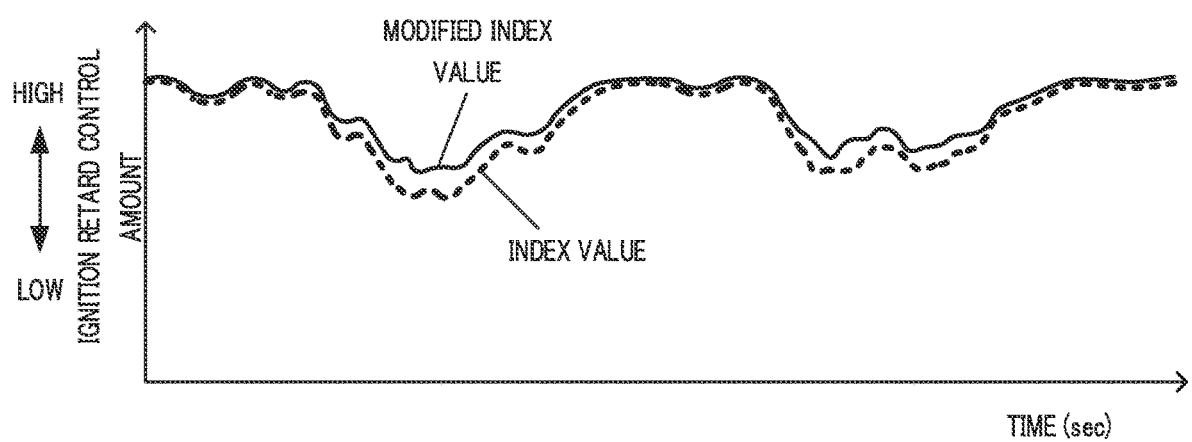
FIG. 3 illustrates an exemplary index value, which indicates an ignition retard control amount in a cylinder, and an exemplary modified index value.

Next, estimation unit 110 calculates the modified index value by adding the correction term to the index value (average value). FIG. 3 illustrates an exemplary index value, which indicates an ignition retard control amount in a cylinder, and an exemplary modified index value.

Next, estimation unit 110 estimates, based on the calculated modified index value, the methane number by referring to a predetermined conversion table. Here, the conversion table refers to a table indicating the relationship between the modified index value and the methane number.

Figure 4:
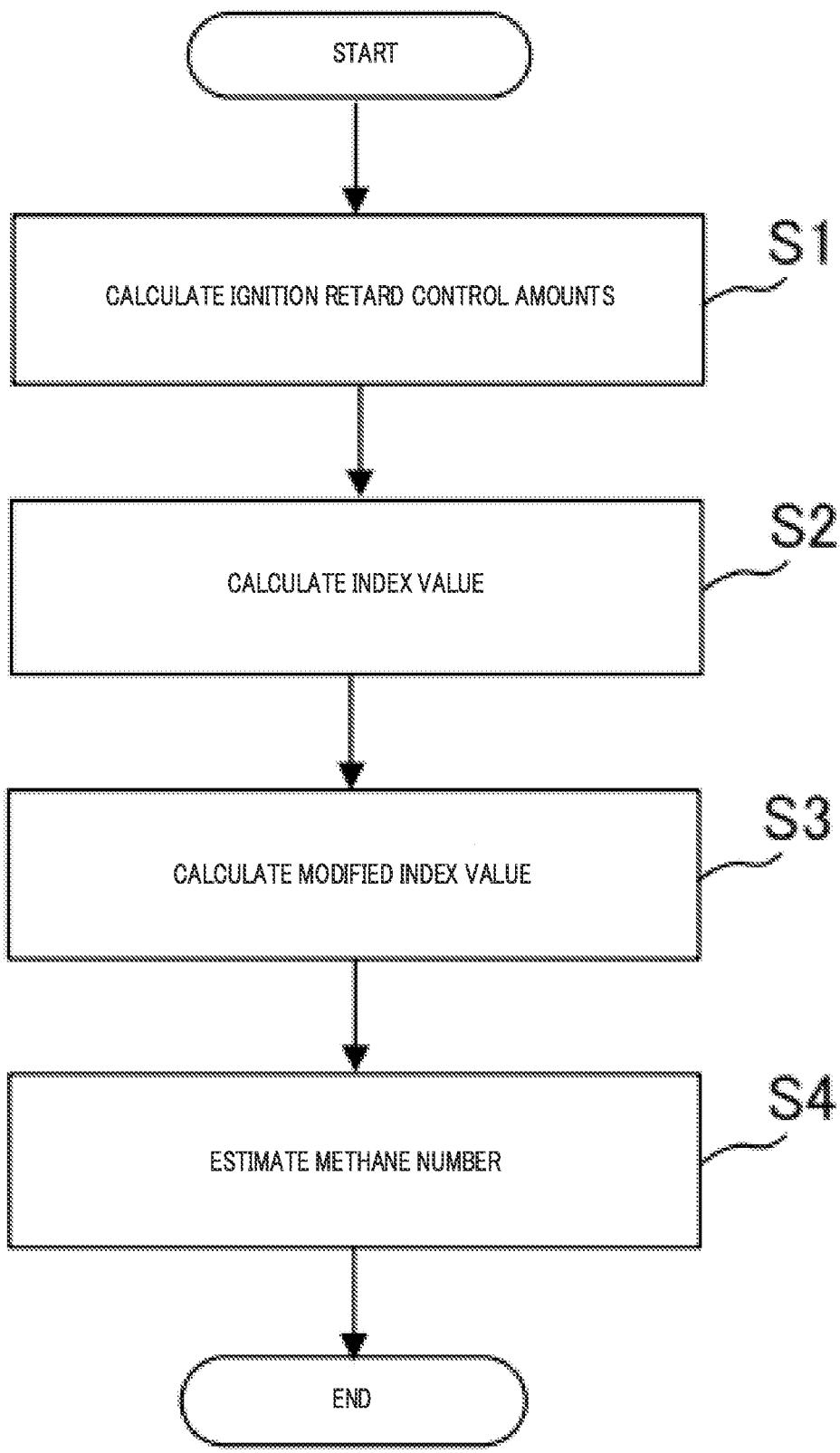
FIG. 4 is a flowchart illustrating an exemplary first estimation method.

FIG. 4 summarizes the flow of the first estimation method described above. For example, the flow in FIG. 4 starts after the start of the engine and is executed for each predetermined time during the operation of the engine.

First, estimation unit 110 calculates ignition retard control amounts (advance values) based on the knocking information (step S1).

Next, estimation unit 110 calculates an index value by calculating an average value of, among the acquired respective advance values (ignition retard control amounts) in the plurality of cylinders, the respective advance values in two or more cylinders, where the respective advance values in the two or more cylinders are lower than the (respective) advance value(s) in the other cylinder(s) among the plurality of cylinders (step S2).

Next, estimation unit 110 calculates, based on the speed information and the load information, the correction term for the index value by referring to the correction map, and calculates the modified index value by adding the calculated correction term to the index value (step S3).

Next, estimation unit 110 estimates, based on the calculated modified index value, the methane number by referring to the predetermined conversion table (step S4).

The methane number estimated in the above-described manner is compared with the threshold by control unit 120.

Next, the second estimation method will be described in detail.

Estimation unit 110 performs preparation processing before executing the second estimation method. Specifically, in a case where the engine in a driven state has stopped, estimation unit 110 acquires and stores the date and time information, the remaining amount information, and the estimated methane number at the time of the engine stop. The estimated methane number to be stored here is the latest methane number estimated by the first estimation method described above. This estimated methane number is a value equal to or less than the initial value (the methane number when the LNG tank is filled with the LNG fuel).

Thereafter, in a case where the engine in a stopped state has restarted, estimation unit 110 acquires the date and time information at the time of the engine restart. Estimation unit 110 then executes the second estimation method as follows.

First, estimation unit 110 calculates, based on the date and time information at the time of the engine stop and the date and time information at the time of the engine restart, the time from when the engine has stopped to when the engine has restarted (in other words, the time during which the engine has been stopped; hereinafter referred to as the engine stop time).

Next, estimation unit 110 determines, based on the calculated engine stop time and the remaining amount indicated in the remaining amount information at the time of the engine stop, a subtraction value by referring to a subtraction map (not illustrated).

The subtraction map is stored in the storage unit (for example, the ROM (not illustrated)) of fuel property determination apparatus 100. The subtraction map is a map indicating the relationship of the engine stop time and the remaining amount with the subtraction value (for example, a table in which the subtraction value is defined correspondingly to the value indicating the engine stop time and the value indicating the remaining amount), and can be obtained by means of experiments and/or simulations. This subtraction map is defined such that the subtraction value is larger as the engine stop time is longer and/or the remaining amount is smaller.

Next, estimation unit 110 estimates the methane number by subtracting the determined subtraction value from the estimated methane number stored at the time of the engine stop (the estimated methane number obtained by the first estimation method).

The methane number estimated in the above-described manner is compared with the threshold by control unit 120.

Figure 5:
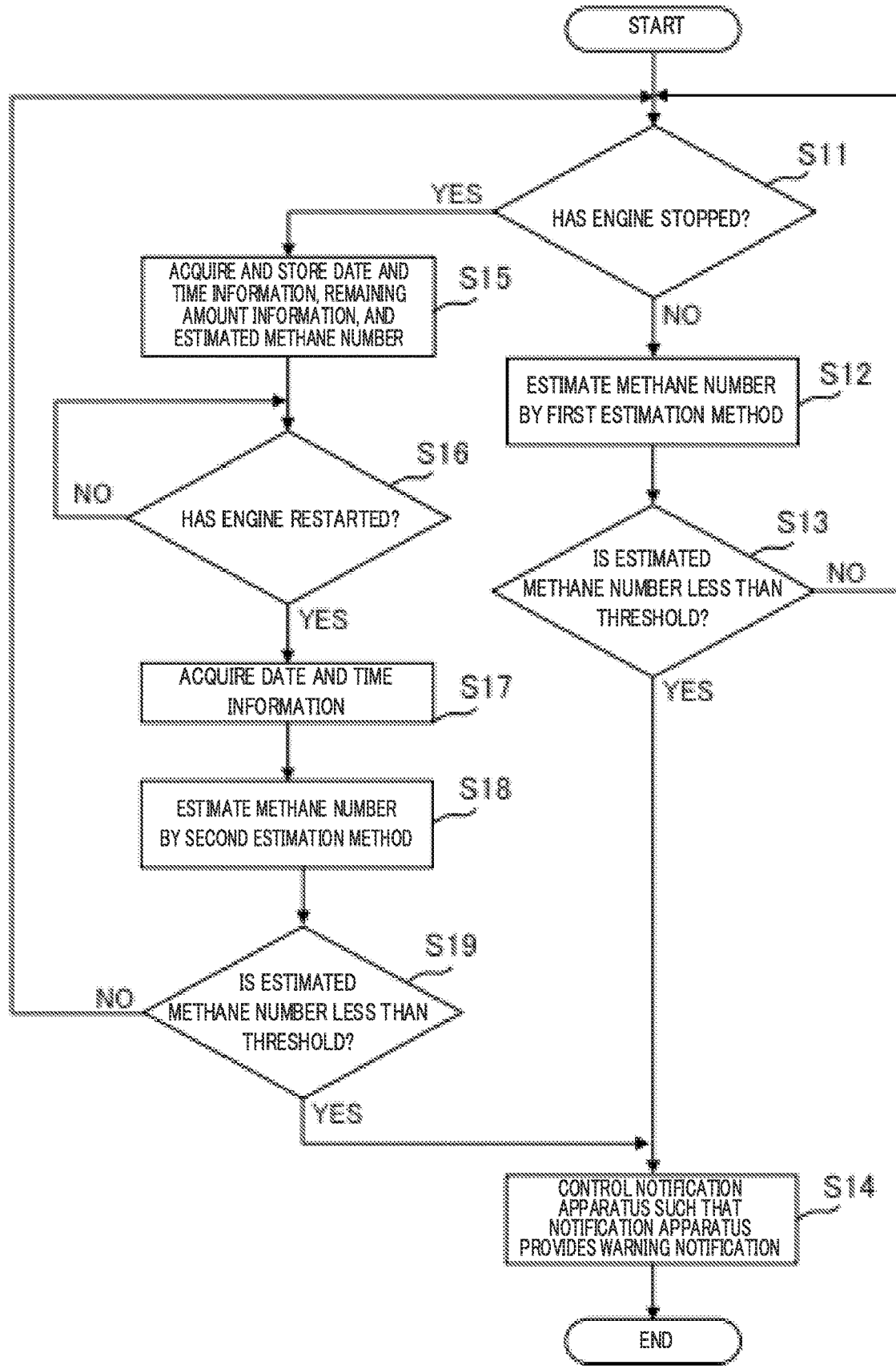
FIG. 5 is a flowchart illustrating exemplary operations of the fuel property determination apparatus according to the embodiment of the present disclosure.

Next, operations of fuel property determination apparatus 100 will be described with reference to FIG. 5. FIG. 5 is a flowchart illustrating exemplary operations of fuel property determination apparatus 100. The flow in FIG. 5 starts, for example, when the engine starts for the first time after the LNG tank is filled with the LNG fuel. Note that, it is configured here as an example that estimation unit 110 determines (detects), based on a predetermined operation by an occupant in the vehicle (for example, turning on/off an engine start switch), whether the engine has started and whether the engine has stopped.

First, estimation unit 110 determines whether the engine that had been started has stopped (step S11).

In a case where the engine has stopped (step S11: YES), the flow proceeds to step S15 to be described later.

In a case where the engine has not stopped (step S11: NO), estimation unit 110 estimates the methane number by the first estimation method described above (step S12).

Next, control unit 120 determines whether the estimated methane number is less than the threshold (step S13).

In a case where the estimated methane number is not less than the threshold (step S13: NO), the flow returns to step S11.

In a case where the estimated methane number is less than the threshold (step S13: YES), control unit 120 controls notification apparatus 60 such that notification apparatus 60 provides the warning notification (step S14). Thus, notification apparatus 60 provides the warning notification, and the user (the occupant in the vehicle) can recognize that a property change has occurred in the LNG fuel.

In a case where the engine has stopped (step S11: YES), estimation unit 110 acquires and stores the date and time information, the remaining amount information, and the estimated methane number (the estimated methane number obtained by the first estimation method) at the time of the engine stop (step S15).

Thereafter, estimation unit 110 determines whether the engine in a stopped state has restarted (step S16).

In a case where the engine has not restarted (step S16: NO), the flow returns to step S16.

In a case where the engine has restarted (step S16: YES), estimation unit 110 acquires the date and time information at the time of the engine restart (step S17).

Next, estimation unit 110 estimates the methane number by the second estimation method described above based on the date and time information, the remaining amount information, and the estimated methane number at the time of the engine stop, the date and time information at the time of the engine restart, and the subtraction map (step S18).

Next, control unit 120 determines whether the estimated methane number is less than the threshold (step S19).

In a case where the estimated methane number is not less than the threshold (step S19: NO), the flow returns to step S11. Note that, in this case, the methane number may be estimated, in the subsequent first estimation method (step S12), based on the methane number estimated by the second estimation method (step S18).

In a case where the estimated methane number is less than the threshold (step S19: YES), control unit 120 controls notification apparatus 60 such that notification apparatus 60 provides the warning notification (step S14). Thus, notification apparatus 60 provides the warning notification, and the user (the occupant in the vehicle) can recognize that a property change has occurred in the LNG fuel.

As described above, fuel property determination apparatus 100 in the present embodiment is an apparatus that determines a component of an LNG fuel stored, as a fuel for an engine, in an LNG tank. Fuel property determination apparatus 100 includes: estimation unit 110 that estimates, in a case where the engine is being driven, a methane number of the LNG fuel by a first estimation method and estimates, in a case where the engine is restarted from a stopped state, the methane number of the LNG fuel by a second estimation method different from the first estimation method; and control unit 120 that controls, in a case where the methane number estimated by the first estimation method or the second estimation method is less than a threshold, notification apparatus 60 such that notification apparatus 60 provides a notification indicating that a property change has occurred in the LNG fuel.

With this feature, the methane number is estimated using separate methods for when the engine is being driven and for when the engine being stopped, and thus, the reliability of the estimated methane number improves, and it is possible to determine more accurately whether a property change has occurred in the LNG fuel. Accordingly, the user can recognize with more appropriate timing that a property change has occurred in the LNG fuel, and can execute measures against the property change (consumption of the LNG fuel, filling of the LNG fuel, or the like).

In addition, the first estimation method makes it possible to set a more appropriate ignition advance based on the estimated methane number. For this mason, it is possible to suppress occurrence of excessive knocking and occurrence of engine malfunction. Further, it is possible to maintain the performance of the engine in an appropriate state.

In addition, in the first estimation method, the respective advance values (ignition retard control amounts) in the plurality of cylinders are acquired, and an average value of, among the acquired respective advance value in the plurality of cylinders, the respective advance values in two or more cylinders, where the respective advance values in the two or more cylinders are lower than the (respective) advance value(s) in the other cylinder(s) among the plurality of cylinders, is calculated as an index value. Since it is possible to surely detect a property change in the LNG fuel thereby, it is possible to improve the certainty of detecting a decrease in the methane number.

In addition, in the first estimate method, the methane number of the LNG fuel is estimated based on the index value corrected based on the engine speed and the engine load (that is, the modified index value described above). Accordingly, the index value is standardized, and thus, the accuracy of the estimation of the methane number can be improved.

Note that, the present disclosure is not limited to the embodiment described above, and various variations can be made without departing from the gist thereof. Hereinafter, variations will be described.

Variation 1

In the embodiment, as the subtraction map used in the second estimation method, a plurality of subtraction maps may be prepared according to the magnitude of the estimated methane number at the time of the engine stop, and the respective subtraction maps may be defined such that the subtraction values differ from each other even with the same remaining amount and the same engine stop time.

Variation 2

In the embodiment, a case where estimation unit 110 corrects the index value based on the correction term or the like and estimates the methane number by using the modified index value obtained thereby has been described as an example, but the present disclosure is not limited thereto. For example, estimation unit 110 may estimate the methane number by using the index value before correction.

Variation 3

In the embodiment, a case where control unit 120 controls notification apparatus 60 has been described as an example, but notification apparatus 60 as well as other apparatuses may be objects to be controlled by control unit 120. For example, in a case where the estimated methane number decreases to a value equal to or less than the threshold and the engine is in a high-load state, control unit 120 may control the respective isolation valves of the LNG fuel supply system and the CNG fuel supply system such that the LNG fuel supply path is closed and the CNG fuel supply path is opened. Since switching from the LNG fuel to the CNG fuel is performed thereby, it is possible to suppress occurrence of excessive knocking and occurrence of engine malfunction.

Variation 4

In the embodiment, a case where notification apparatus 60 is a display lamp provided in the vehicle interior has been described as an example, but the present disclosure is not limited thereto. For example, notification apparatus 60 may be a display that performs displaying of an image indicating that a property change has occurred in the LNG fuel (an example of the warning notification), or may be a speaker that outputs a voice indicating that a property change has occurred in the LNG fuel (an example of the warning notification). Further, both image displaying and voice output may be performed as the warning notification.

Variation 5

In the embodiment, a case where fuel property determination apparatus 100 is mounted in a vehicle has been described as an example, but the present disclosure is not limited thereto. Fuel property determination apparatus 100 may be mounted in a moving body other than a vehicle (for example, a ship or the like) or in a machine including a stationary engine, or the like.

Variation 6

In the embodiment, a case where the engine load is acquired by using torque sensor 50 has been described as an example, but the present disclosure is not limited thereto. For example, fuel property determination apparatus 100 may estimate the engine load based on the intake manifold pressure. In this case, the intake manifold pressure is detected by a pressure sensor.

The present application is based on a Japanese Patent Application (Japanese Patent Application No. 2021-170415), filed on Oct. 18, 2021, the content of which is incorporated herein by reference.

INDUSTRIAL APPLICABILITY

The fuel property determination apparatus and the vehicle in the present disclosure are useful in a case where liquefied natural gas containing a plurality of components with boiling points different from each other is used as a fuel for an engine.

REFERENCE SIGNS LIST

10 Time measurement apparatus
20 Remaining amount sensor
30 Knock sensor
40 Crank angle sensor
50 Torque sensor
60 Notification apparatus
100 Fuel property determination apparatus
110 Estimation unit
120 Control unit

The invention claimed is:

1. A fuel property determination apparatus that determines a component of liquefied natural gas stored in a tank as a fuel for an engine, the fuel property determination apparatus comprising a processor configured to:
   when the engine is being driven, calculate an ignition retard control amount for avoiding knocking in the engine and estimate a first methane number of the liquefied natural gas based on an index value indicating the ignition retard control amount;
   when the engine is restarted from a stopped state, estimate a second methane number of the liquefied natural gas based on the first methane number, a remaining amount of the liquefied natural gas when the engine stops, and a stop time of the engine; and
   when the first methane number or the second methane number is less than a threshold, notify that a property change has occurred in the liquefied natural gas.

2. The fuel property determination apparatus according to claim 1, wherein
   the processor is further configured to cause a display lamp to flicker at predetermined time intervals to notify a result of the determination, the display lamp being provided in a vehicle interior of a vehicle in which the engine is mounted.

3. A vehicle, comprising the fuel property determination apparatus according to claim 1.

* * * * *